United States Patent [19]

Saunders

[11] Patent Number: 5,669,925
[45] Date of Patent: Sep. 23, 1997

[54] SOFT TISSUE GRAFT INTRODUCER

[76] Inventor: Michael R. Saunders, 9728 Snowberry Way, Orangevale, Calif. 95662

[21] Appl. No.: 597,176

[22] Filed: Feb. 6, 1996

[51] Int. Cl.⁶ .................................................. A61F 11/00
[52] U.S. Cl. ............................. 606/108; 128/657; 604/93
[58] Field of Search .................................. 606/108, 132, 606/194, 195, 198, 127, 191; 604/280, 281, 93, 160, 164, 174; 128/657, 772

[56] References Cited

U.S. PATENT DOCUMENTS

| | | | |
|---|---|---|---|
| 4,552,554 | 11/1985 | Gould et al. | 604/280 |
| 4,578,061 | 3/1986 | Lemelson | 604/164 |
| 4,928,693 | 5/1990 | Goodin et al. | 604/280 |
| 5,059,177 | 10/1991 | Towne et al. | 606/194 |
| 5,190,552 | 3/1993 | Kelman . | |
| 5,290,295 | 3/1994 | Querals et al. . | |
| 5,325,848 | 7/1994 | Adams et al. . | |
| 5,358,496 | 10/1994 | Ortiz et al. . | |
| 5,366,473 | 11/1994 | Winston et al. . | |
| 5,370,109 | 12/1994 | Cuny | 606/198 |
| 5,378,241 | 1/1995 | Haindl | 604/164 |
| 5,409,478 | 4/1995 | Gerry et al. . | |
| 5,415,664 | 5/1995 | Pinchuk . | |
| 5,441,044 | 8/1995 | Tovey et al. . | |
| 5,542,434 | 8/1996 | Imran et al. | 604/281 |

OTHER PUBLICATIONS

The Paramax ACL Guide System Surgical Technique, Linvatec Concept Arthoscopy, 1992, Linvatec Corporation.

Primary Examiner—Robert A. Hafer
Assistant Examiner—Justine Yu
Attorney, Agent, or Firm—John P. O'Banion

[57] ABSTRACT

A soft tissue graft introducer for use in endoscopic surgeries, which comprises a tubular sheath with a guide wire slidably disposed therein. The guide wire includes a retractable tip at its distal end, and a transverse bend adjacent the retractable tip. A fixed tip adjacent the distal end of the tubular sheath includes a base with an angled surface. When the retractable tip of guide wire is slidably extended or retracted from the tubular sheath, the retractable tip also moves laterally relative to the fixed tip due to the transverse bend in the guide wire and the angled face on the base of the fixed tip.

16 Claims, 4 Drawing Sheets

SOFT TISSUE GRAFT INTRODUCER

BACKGROUND OF THE INVENTION

1. Field of the Invention

This invention pertains generally to devices and methods for manipulation of tissue during endoscopic surgery, and more particularly to an apparatus for introduction of soft tissue grafts during arthroscopic surgical procedures.

2. Description of the Background Art

The development of arthroscopic, laparoscopic, and other endoscopic surgeries has reduced the use of more intrusive surgical operations wherein large surgical incisions are made to provide access to surgical objectives. Endoscopic surgical techniques require surgical instruments suitable for use through relatively small surgical incisions, and a variety of such instruments have been developed. For example, endoscopic tissue manipulators with expandable, resilient ribbon or wire frame structures contained in elongated tubes or sheaths are known. The introduction of tissue grafts in endoscopic procedures generally employs devices wherein a tissue sample is held by one or more forks or tines associated with an elongated, non-retractable member. The use of devices with hollow tubes or sheaths which contain an elongated wire applicator or other resilient member have also been disclosed.

A particular problem associated with the introduction or insertion of soft tissue grafts during endoscopic procedures, such as ACL reconstruction, is that difficulty is frequently encountered in disengaging or removing the graft from the surgical instrument when the graft is in place. In the presently known background art devices used for introduction of grafts, the graft tissue tends to stick onto the end of the fork or retractable member and is not readily removed, leading to delays, inconvenience, and non-optimal graft placement.

Accordingly, there is a need for a soft tissue introducer apparatus which provides for quick and facile disengagement of tissue grafts when the graft is in place. The present invention satisfies this need, as well as others, and generally overcomes the deficiencies found in the background art.

The foregoing reflects the state of the art of which the applicant is aware and is tendered with the view toward discharging applicant's acknowledged duty of candor in disclosing information which may be pertinent in the examination of this application. It is respectfully stipulated, however, that none of the background art teaches or renders obvious applicant's claimed invention.

SUMMARY OF THE INVENTION

The present invention pertains generally to an apparatus for introduction of soft tissue grafts during endoscopic surgical operations which is particularly well suited for arthroscopic surgery. In general terms, the invention comprises a tubular sheath having a fixed tip associated with a distal end, and a guide wire slidably disposed within the sheath. The guide wire includes a retractable tip at a distal end, and a transverse bend in the wire adjacent to the retractable tip. The fixed tip on the sheath includes an angled base which serves as a lateral guide for the guide wire. The invention also preferably includes means for retracting and extending the guide wire relative to the sheath.

By way of example and not of limitation, the sheath is of generally elongated configuration, and includes a first opening adjacent the distal end for accommodating the retractable tip of the guide wire. The sheath also preferably includes a second opening adjacent the distal end for accommodating the transverse bend in the guide wire. The fixed tip is generally coupled to the distal end of the sheath and is positioned off center from a longitudinal axis extending between the proximal and distal ends of the sheath. The base of the fixed tip includes an angled surface which serves as a lateral guide for the guide wire. The proximal end of the sheath is coupled to a housing which reversibly engages a handle member, preferably by threads or other conventional means. The guide wire preferably includes a proximal end which extends through the housing and into the handle member. The means for retracting and extending the guide wire are preferably associated with the handle or the housing. The retracting and extending means is preferably a manually operable arrangement wherein a thumb slide located within a slot in the handle or housing and associated with the proximal end of the guide wire is used to slidably extend and retract the guide wire within the sheath.

The invention is utilized generally by securing a tissue graft onto the retractable tip of the guide wire while the retractable tip is in an extended position. The tissue graft is moved into place, the instrument is partially retracted (enough to clear the tips from the graft), and the retractable tip is retracted by manually operating the thumb slide in the handle, which slides or retracts the guide wire within the sheath. The transverse bend and angled surface of the base of the fixed tip cause the retractable tip to move laterally towards the fixed tip as the retractable tip is retracted. The fixed tip then pushes the tissue graft off of the retractable tip in the desired location.

An object of the invention is to provide a soft tissue graft introducer which allows quick and facile disengagement of tissue grafts.

Another object of the invention is to provide a soft tissue graft introducer which is inexpensive to manufacture and is easy to use.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
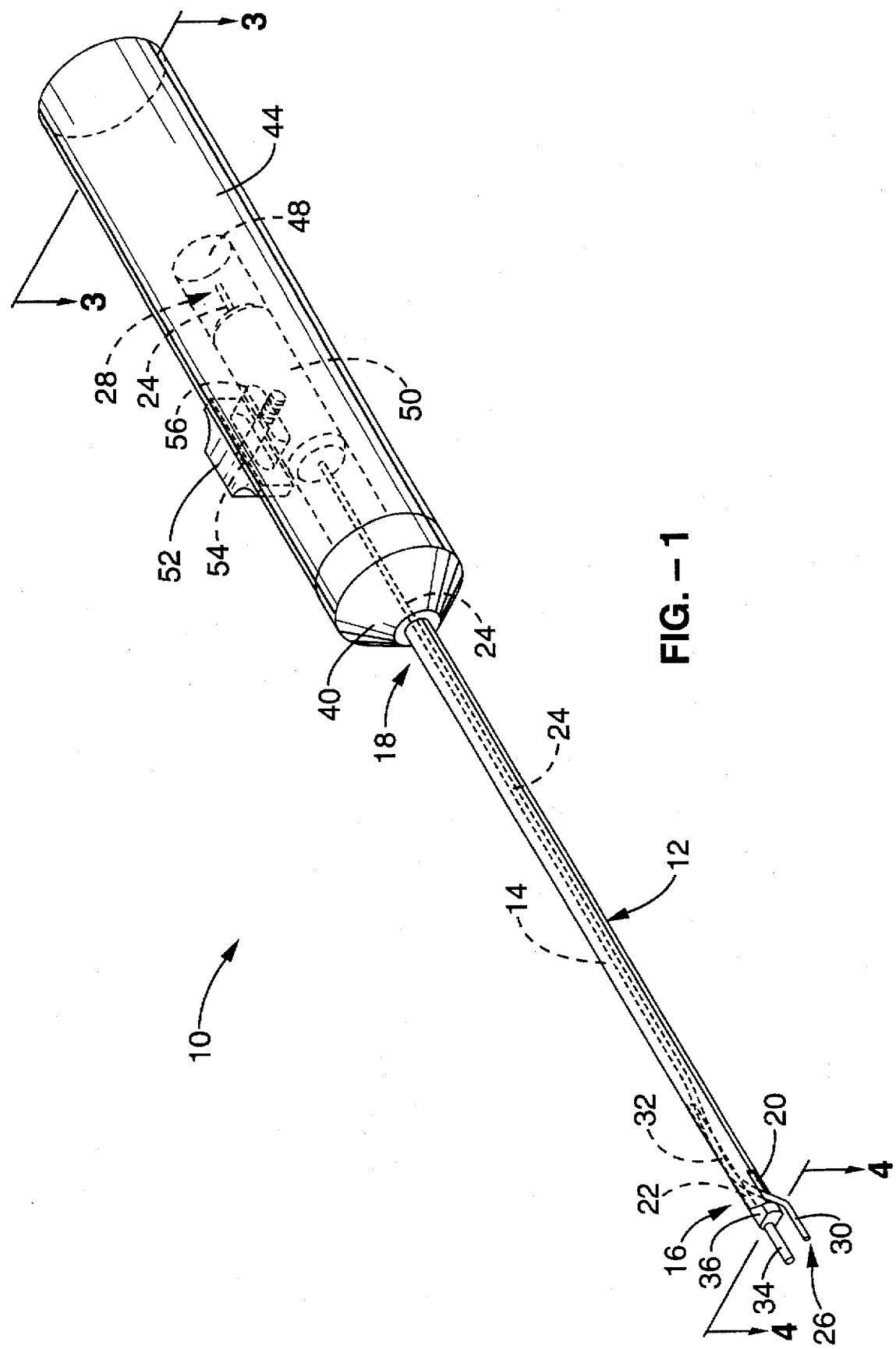
FIG. 1 is a perspective view of a soft tissue graft introducer in accordance with the present invention.

Referring more specifically to the drawings, for illustrative purposes the present invention is embodied in the apparatus which is generally shown in FIG. 1 through FIG. 5. It will be appreciated that the apparatus may vary as to configuration and as to details without departing from the basic concepts as disclosed herein. The invention is particularly well suited for use in arthroscopic reconstruction procedures or operations. However, the invention may be utilized in a variety of endoscopic surgical procedures, as will be readily apparent to persons of ordinary skill in the art.

Referring now to FIG. 1 through FIG. 5, a soft tissue graft introducer 10 in accordance with the present invention is generally shown. The invention includes a tubular sheath or hollow tube 12, preferably of elongated configuration and generally cylindrical cross-section as shown, with a longitudinal bore 14 extending therethrough. Tubular sheath 12 includes a distal end 16 and a proximal end 18. A first aperture or opening 20 is included in tubular sheath adjacent to distal end 16, and a second aperture or opening 22 is also generally included adjacent distal end 16. Second opening 22 is preferably positioned opposite first opening 20.

A guide wire 24 is slidably disposed within bore 14 of tubular sheath 12. Guide wire 24 is generally elongated and resilient, and preferably has a cylindrical cross section. Guide wire 24, however, may alternatively be in the form of an elongated, resilient ribbon or strip. Guide wire 24 includes a distal end 26 and a proximal end 28. A sliding, moving, or retractable tip 30 is included at the distal end 26 of guide wire 24. A transverse bend or crook 32 is included on guide wire 24, with transverse bend 32 generally adjacent to distal end 26 and retractable tip 30. Retractable tip 30 extends through first opening 20 in tubular sheath 12, and transverse bend 32 in guide wire 24 is accommodated by second opening 22. Second opening 22 in tubular sheath 12 is preferably elongated in shape or slot-like in order to accommodate transverse bend 32 in guide wire 24.

A generally cylindrical fixed or stationary tip 34 is coupled to the distal end 16 of tubular sheath 12, and is preferably positioned off-center relative to the longitudinal axis of tubular sheath 12, with the longitudinal axis generally defined by longitudinal bore 14 in tubular sheath 12.

Means for laterally guiding retractable tip 30 of guide wire 24 are associated with fixed tip 34, and preferably comprise an angled base 36, adjacent fixed tip 34. Base 36 is structured and configured to include an angled face 38 (see FIG. 4 and FIG. 5), with face 38 angularly offset by about 45° relative to the longitudinal axis of tubular sheath 12. The lateral guiding means may alternatively comprise an equivalent curved or angled feature associated with distal end 16 of tubular sheath 12. The lateral guiding of retractable tip 30 of guide wire 24 is discussed further below.

Figure 2:
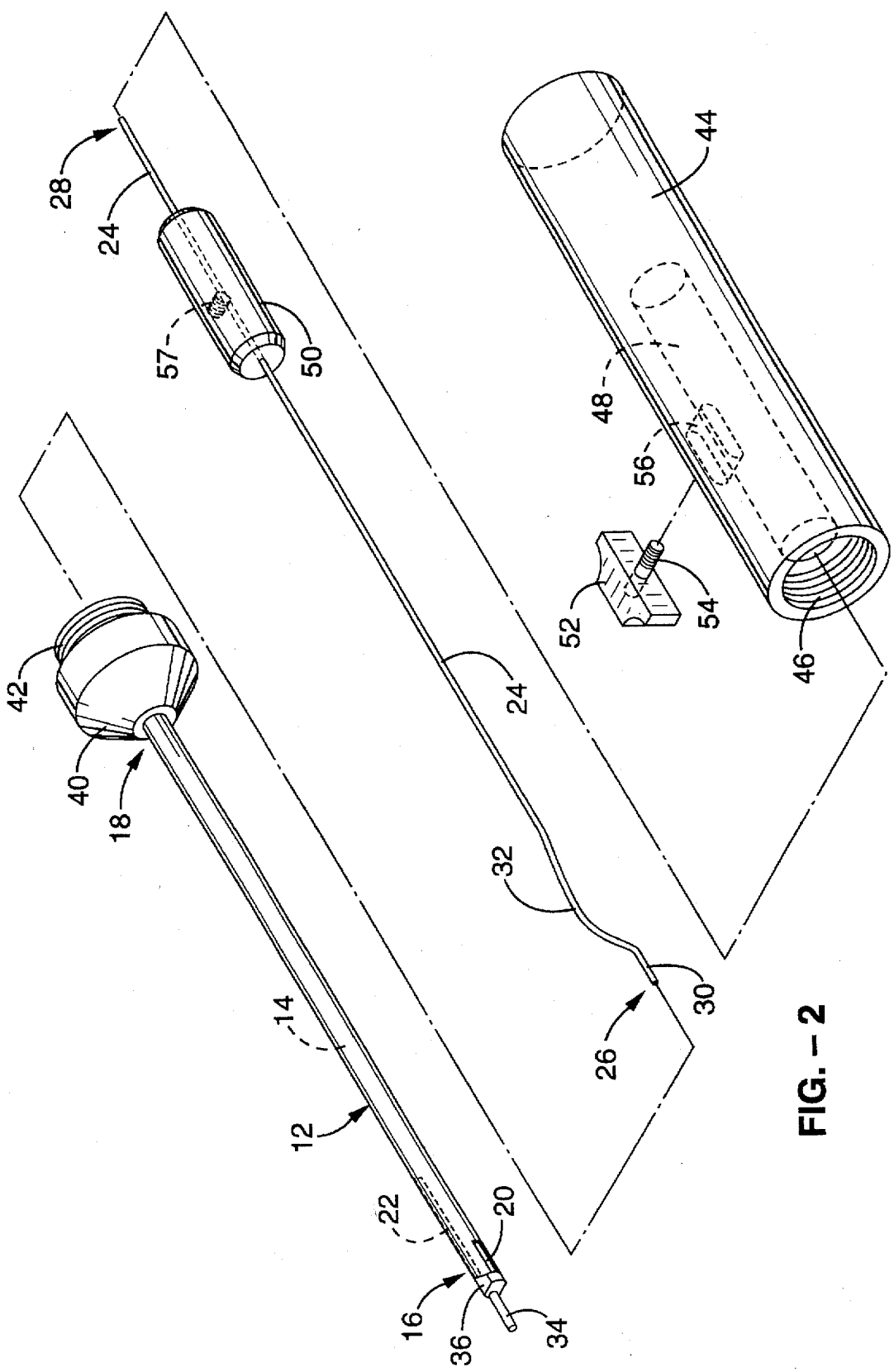
FIG. 2 is an exploded view of the soft tissue graft introducer of FIG. 1.

Referring more specifically to FIG. 2, a housing 40 is coupled to the proximal end 16 of tubular sheath 12 using adhesives or other conventional coupling means. Housing 40 includes an externally threaded portion 42. A handle 44 is preferably included with the soft tissue graft introducer 10, with handle 44 having an internally threaded socket 46 which reversibly engages the threaded portion 42 on housing 40. Handle 44 includes a generally longitudinal bore 48 which accommodates the proximal end 28 of guide wire.

The invention preferably includes means for retracting and extending guide wire 24 within bore 14 of tubular sheath 12. In the preferred embodiment, the retracting and extending means is associated with the proximal end 28 of guide wire 24, and comprises a slide member 50 coupled to guide wire 24 by standard means adjacent distal end 28. Slide member 50 is slidably accommodated by bore 48 in handle 44. A thumb slide 52 is coupled to slide member 50 by threaded pin 54, with pin 54 extending through a slot 56 in handle 44 and into a threaded opening 57 in slide member 50.

Other standard retracting and extending means for guide wire are also contemplated for use with the invention. For example, an alternative, manually operable retracting and extending means for use with the invention may comprise a pistol grip-like handle with a pivoting, manually operable trigger portion or lever pivotally associated with proximal end 28 of guide wire 24 such that actuation of the trigger portion with an index finger causes slidably moves guide wire 24 within sheath 12.

Figure 3:
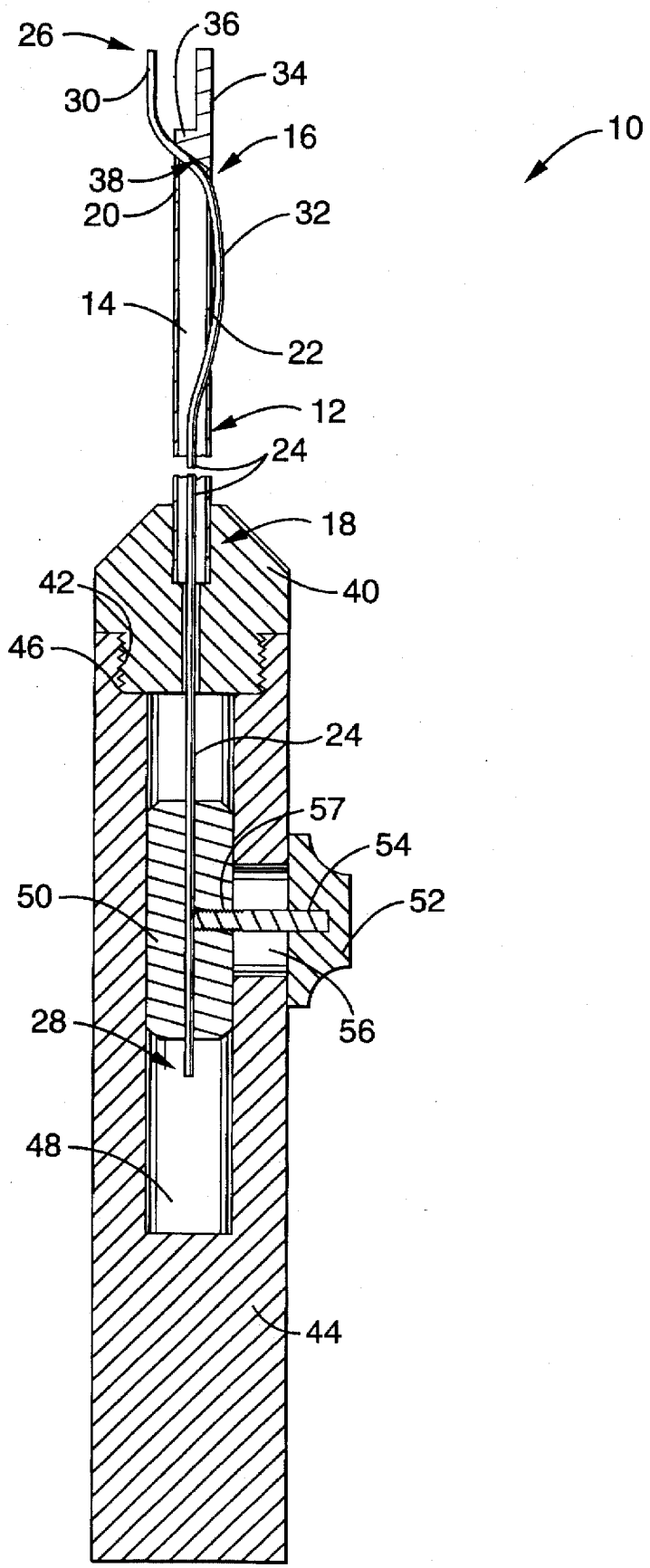
FIG. 3 is a cross-sectional view of the soft tissue graft introducer shown in FIG. 1 taken through line 3—3.

As shown in FIG. 1 through FIG. 3, the retracting and extending means of the invention is generally associated with handle 44. It is also contemplated, however, that the retracting and extending means could alternatively be associated with housing 40, if housing 40 were elongated relative to the configuration shown, and slot 56 is then located within housing 40 rather than in handle 44 as shown.

The invention may be assembled generally by slidably inserting guide wire 24 into longitudinal bore 14 of tubular sheath 12 and positioning guide wire 24 therein such that retractable tip 30 extends out through first opening 20 adjacent distal end 16 of tubular sheath 12, with transverse bend 32 extending through second opening 22, and with slide member 50 adjacent to threaded portion 46 of housing 40 and proximal end 18 of tubular sheath 12. Handle 44 is coupled to housing 40 by engaging threaded portion 42 of housing 40 within threaded socket 46. Thumb slide 52 is coupled to slide member 50 by threading pin 54 into slide member 50 through slot 56 in handle 44 and tightening pin 54 until it abuts guide wire 24 tightly so as to hold guide wire 24 in place.

Figure 4:
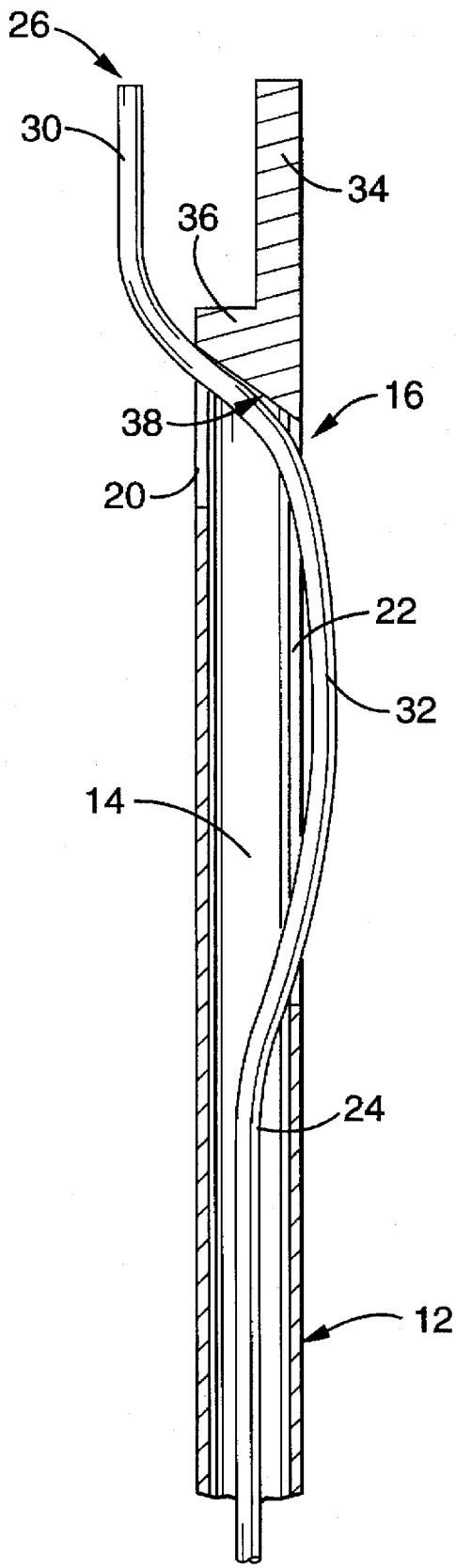
FIG. 4 is a partial cross section of the retractable tip, fixed tip, and distal portion of the sheath and guide wire shown in FIG. 1, taken through line 4—4.
Figure 5:
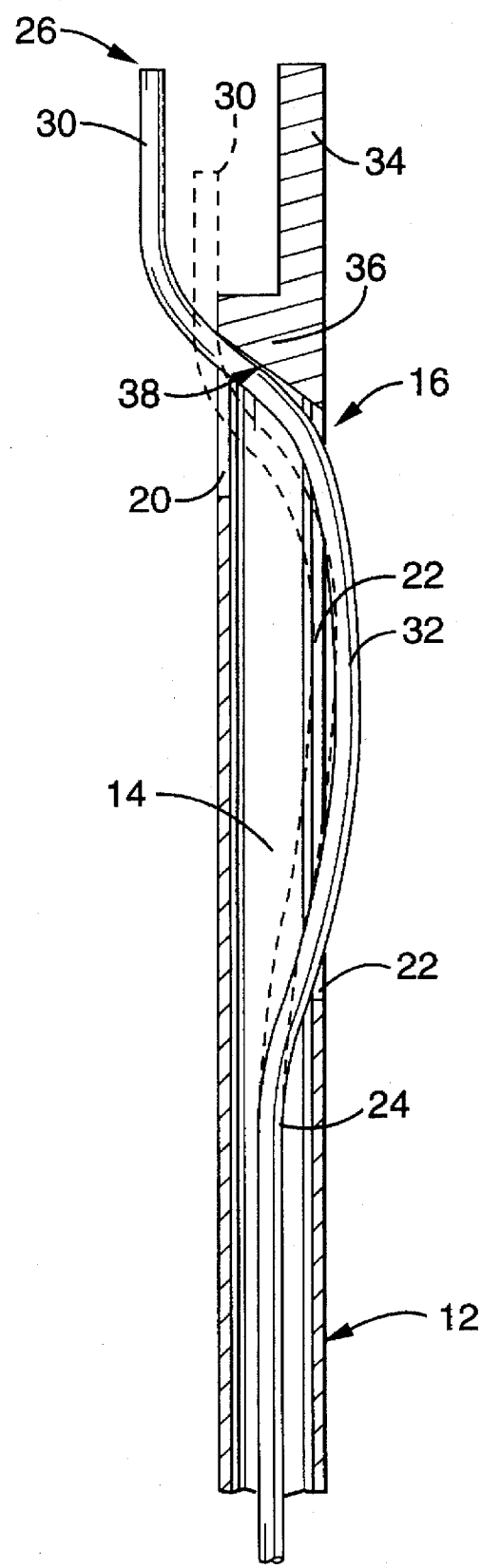
FIG. 5 is the partial cross section of FIG. 4 showing diagrammatically the moved position of the retractable tip and transverse bend of the guide wire of the invention.

Referring now to FIG. 4 and FIG. 5 as well as FIG. 1 through FIG. 3, the range of motion of retractable tip 30 of guide wire 24 relative to fixed tip 34 is illustrated. When thumb slide 52 is manually moved upward or away from handle 44 and towards housing 40, retractable tip 30 of guide wire 24 slidably extends or moves outward relative to fixed tip 34 and first opening 20. As thumb slide 52 is moved downward or towards handle 44 and away from housing 40, retractable tip 30 on guide wire 24 is retracted or otherwise moves inward towards fixed tip 34 and first opening 20, as shown generally in phantom in FIG. 5.

Upon extension or retraction of guide wire 24 by sliding guide wire 24 within bore 14 of sheath 12, lateral motion is imparted to retractable tip 30. This lateral motion is provided because transverse bend 32 moves laterally due to second opening 22, which allows transverse bend 32 to move laterally relative to sheath 12, and due to angled face 38 on base 36 which serves as guide means. The range of lateral motion can be seen most clearly in FIG. 4 and FIG. 5. Thus, as guide wire 24 and retractable tip 30 are extended, retractable tip 30 moves laterally away from fixed tip 34, and when guide wire 24 and retractable tip 30 are retracted, retractable tip 30 moves laterally towards fixed tip. The lateral motion of retractable tip 30 relative to fixed tip 34 provides for quick, easy, and accurate placement of tissue grafts with the invention as described below.

The soft tissue graft introducer 10 of the present invention can be utilized in several different ways. One use is to retract the retractable tip 30 and impale or "skewer" a tissue graft on the fixed tip 34. Once the tissue graft is in position, the apparatus is then withdrawn. Another use would be to place a tissue graft between fixed tip 34 and retractable tip 30 when retractable tip is in the extended position, thereby "hooking" the tissue graft with the apparatus. When the tissue graft is positioned for introduction, the surgeon would withdraw the apparatus slightly to clear the graft from the apparatus. Retractable tip 30 is then retracted as described above and the apparatus is withdrawn. A still further use would be to clamp a tissue graft between retractable tip 30 and fixed tip 34 with retractable tip 30 in the retracted position. When the tissue graft is properly positioned in the desired area, the surgeon extends retractable tip 30, withdraws the apparatus slightly to clear the tissue graft, and retracts the retractable tip 30 so that the apparatus can be withdrawn. A still further use would be for insertion of a bone-tendon-bone graft, as could be harvested from the central one-third of the patellar tendon. Here, the apparatus is hooked over a single suture that is placed through the bone block via a drill hole and inserted into the femoral tunnel. The retractable tip 30 is retracted against the ligament at a bone/ligament juncture. The apparatus and graft are then inserted into the delivery area. Retractable tip 30 is then extended to release the graft, the apparatus is withdrawn slightly to clear the graft, retractable tip 30 is retracted, and the apparatus is withdrawn. Those skilled in the art will readily appreciate the vast number of surgical procedures which are possible with the present invention.

The soft tissue graft introducer 10 comprising the invention is preferably fabricated from materials suitable for sterilization by autoclaving, such as metal or metal alloys and/or synthetic polymers which are sufficiently heat-stable to withstand repeated autoclaving. Tubular sheath 12 preferably is substantially rigid in construction, although a resilient tubular sheath may be utilized with the invention. Guide wire 24 preferably comprises resilient metal or metal alloy.

Accordingly, it will be seen that the present invention provides a soft tissue graft introducer which allows quick and easy release of tissue grafts and accurate placement of tissue grafts during endoscopic surgical procedures such as arthroscopic reconstructions. Although the description above contains many specificities, these should not be construed as limiting the scope of the invention but as merely providing illustrations of some of the presently preferred embodiments of this invention. Thus, the scope of the invention should be determined by the appended claims and their legal equivalents.

What is claimed is:
1. A soft tissue graft introducer, comprising:
 (a) a tubular sheath having proximal and distal ends;
 (b) a guide wire having proximal and distal ends, said guide wire slidably disposed in said sheath;
 (c) said guide wire including a retractable tip at said distal end of said guide wire, said retractable tip of said guide wire extending through a first opening in said sheath positioned adjacent said distal end of said sheath;
 (d) said guide wire including a transverse bend adjacent said distal end of said guide wire, said transverse bend of said guide wire extending through a second opening in said sheath positioned adjacent said distal end of said sheath, said second opening positioned longitudinally between said first opening and said proximal end of said sheath;
 (e) said sheath having a fixed tip at said distal end of said sheath; and
 (f) guide means positioned adjacent said fixed tip for guiding said retractable tip laterally relative to said fixed tip upon extension or retraction of said guide wire, said guide means positioned between said first and second openings in said sheath.

2. A soft tissue graft introducer as recited in claim 1, further comprising means for retracting and extending said guide wire within said sheath.

3. A soft tissue graft introducer as recited in claim 1, further comprising a handle associated with said proximal end of said sheath.

4. A soft tissue graft introducer according to claim 1, wherein said guide means comprises an angled base associated with said fixed tip.

5. A soft tissue graft introducer as recited in claim 1, wherein said fixed tip is positioned off-center relative a longitudinal axis extending between said proximal and distal ends of said sheath.

6. A soft tissue graft introducer, comprising:
 (a) a tubular sheath having proximal and distal ends, said sheath including first and second openings adjacent said distal end, said second opening positioned longitudinally between said first opening and said proximal end of said sheath;
 (b) a guide wire having proximal and distal ends, said guide wire slidably disposed within said sheath;
 (c) said guide wire having a retractable tip at said distal end of said guide wire, said retractable tip extending through said first opening in said sheath;
 (d) said guide wire including a transverse bend adjacent said distal end of said guide wire, said second opening accommodating said transverse bend;
 (e) said sheath having a fixed tip at said distal end of said sheath; and
 (f) said fixed tip including an angled base positioned between said first and second openings in said sheath.

7. A soft tissue graft introducer as recited in claim 6, further comprising means for retracting and extending said guide wire within said sheath, said retracting and extending means associated with said proximal end of said guide wire.

8. A soft tissue graft introducer as recited in claim 6, further comprising a handle associated with the proximal end of said sheath.

9. A soft tissue graft introducer according to claim 6, wherein said base includes an angled surface, said angled surface adjacent said guide wire, said angled surface facing said guide wire.

10. A soft tissue graft introducer as recited in claim 6, wherein said fixed tip is positioned off-center relative to a longitudinal axis extending between said distal and proximal ends of said sheath.

11. A soft tissue graft introducer, comprising:
 (a) an elongated tubular sheath, said sheath having a longitudinal bore, said sheath including proximal and distal ends, said sheath including first and second openings adjacent said distal end of said sheath, said first opening positioned opposite said second opening, said second opening positioned longitudinally between said first opening and said proximal end of said sheath;
 (b) a guide wire, said guide wire slidably disposed within said sheath, said guide wire having proximal and distal ends;
 (c) said guide wire including a retractable tip at said distal end of said guide wire, said retractable tip extending through said first opening in said sheath;
 (d) said guide wire including a transverse bend adjacent said distal end of said guide wire, said second opening in said sheath accommodating said transverse bend;
 (e) said sheath having a fixed tip at said distal end of said sheath;
 (f) said fixed tip including an angled base, said base positioned to laterally guide said guide wire, said base including an angled surface, said angled surface adjacent said guide wire, said angled surface facing said guide wire, said angled surface positioned between said first and second openings in said sheath; and (g) means for retracting and extending said guide wire in said sheath, said retracting and extending means associated with said proximal end of said guide wire.

12. A soft tissue graft introducer as recited in claim 11, wherein said sheath includes a housing portion adjacent its proximal end.

13. A soft tissue graft introducer as recited in claim 12, further comprising a handle, said handle threadably engaging said housing on said sheath.

14. A soft tissue graft introducer as recited in claim 13, wherein said retracting and extending means is manually operated.

15. A soft tissue graft introducer as recited in claim 13, wherein said retracting and extending means is associated with said handle.

16. A soft tissue graft introducer as recited in claim 11, wherein said fixed tip is positioned off-center relative to a longitudinal axis extending between said proximal and distal ends of said sheath.

* * * * *